US011833338B2

(12) United States Patent
Franke et al.

(10) Patent No.: US 11,833,338 B2
(45) Date of Patent: Dec. 5, 2023

(54) INJECTOR DEVICE

(71) Applicant: Sanofi, Paris (FR)

(72) Inventors: Beate Franke, Frankfurt am Main (DE); Ulrich Brueggemann, Bridgewater, NJ (US); Jeff Kablik, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/152,513

(22) Filed: Jan. 10, 2023

(65) Prior Publication Data

US 2023/0158254 A1 May 25, 2023

Related U.S. Application Data

(62) Division of application No. 16/768,246, filed as application No. PCT/EP2018/083181 on Nov. 30, 2018, now Pat. No. 11,577,032.

(30) Foreign Application Priority Data

Dec. 1, 2017 (EP) .................................... 17306675

(51) Int. Cl.
*A61M 5/32* (2006.01)
*A61M 5/315* (2006.01)
*A61M 5/34* (2006.01)

(52) U.S. Cl.
CPC ...... *A61M 5/3287* (2013.01); *A61M 5/31513* (2013.01); *A61M 5/3202* (2013.01); *A61M 5/347* (2013.01); *A61M 2005/3289* (2013.01)

(58) Field of Classification Search
CPC .......... A61M 5/285; A61M 2005/2488; A61M 2005/2013; A61M 39/18; A61M 2005/3267; A61M 2005/2474
See application file for complete search history.

(56) References Cited

U.S. PATENT DOCUMENTS 3,967,621 A 7/1976 Schwarz
4,976,701 A 12/1990 Ejlersen et al.
(Continued)

FOREIGN PATENT DOCUMENTS

CN 104955503 9/2015
CN 105517599 4/2016
(Continued)

OTHER PUBLICATIONS

International Search Report and Written Opinion in International Appln. No. PCT/EP2018/083181, dated Feb. 20, 2019, 8 pages.
(Continued)

*Primary Examiner* — Katherine H Schwiker
*Assistant Examiner* — Rachel T. Smith
(74) *Attorney, Agent, or Firm* — Fish & Richardson P.C.

(57) ABSTRACT

An injector device includes a housing and a cartridge having a reservoir for medicament. The injector device further includes a needle unit comprising a needle, and an actuator. The needle unit is movably mounted to the housing and, prior to use of the injector device the reservoir, is sealed from the needle. The actuator is configured to move the needle unit into engagement with the cartridge such that the needle is moved into fluid communication with the reservoir. A thread is arranged to cause rotation of the needle unit as the needle unit moves into engagement with the cartridge.

19 Claims, 8 Drawing Sheets

(56) References Cited

U.S. PATENT DOCUMENTS

2013/0150801 A1 6/2013 Ekman et al.
2018/0117240 A1* 5/2018 Archilla .............. A61M 5/3271
2020/0338277 A1 10/2020 Franke et al.

FOREIGN PATENT DOCUMENTS

| CN | 106102801 | 11/2016 |
| CN | 106456892 | 2/2017 |
| EP | 3106190 | 12/2016 |
| FR | 2278350 | 2/1976 |
| WO | WO 2014/118106 | 8/2014 |
| WO | WO 2015/004052 | 1/2015 |
| WO | WO 2015/140262 | 9/2015 |
| WO | WO 2015/144870 | 10/2015 |
| WO | WO 2016/173895 | 11/2016 |
| WO | WO 2017/089277 | 6/2017 |
| WO | WO 2017/089284 | 6/2017 |

OTHER PUBLICATIONS

International Preliminary Report and Written Opinion in International Appln. No. PCT/EP2018/083181, dated Jun. 2, 2020, 6 pages.

* cited by examiner

INJECTOR DEVICE

CROSS REFERENCE TO RELATED APPLICATIONS

The present application is a divisional application of U.S. patent application Ser. No. 16/768,246, filed May 29, 2020, which is the national stage entry of International Patent Application No. PCT/EP2018/083181, filed on Nov. 30, 2018, and claims priority to Application No. EP 17306675.4, filed on Dec. 1, 2017, the disclosures of which are incorporated herein by reference.

TECHNICAL FIELD

The present disclosure relates to an injector device for a medicament.

BACKGROUND

Cartridge injection devices, for example cartridge autoinjectors, typically have a sealed cartridge that contains a medicament and a needle that is initially separated from the cartridge. An initiation movement moves the cartridge and needle together so that the needle pierces the cartridge. A plunger can then be moved into the cartridge to dispense medicament through the needle for injection to a user.

SUMMARY

This disclosure relates to an injector device that comprises a housing, a cartridge having a reservoir for medicament, a needle unit comprising a needle, the needle unit being movably mounted to the housing and wherein prior to use of the injector device the reservoir is sealed from the needle, a needle sleeve that is slidably mounted to the housing such that the needle sleeve slides into the housing during use of the injector device, the needle sleeve being configured to engage the needle unit and push the needle unit into engagement with the cartridge such that the needle is moved into fluid communication with the reservoir, and a thread adapted to cause rotation of the needle unit as the needle unit is pushed into engagement with the cartridge.

The thread may be disposed between the needle unit and the housing and/or the cartridge. For example, the thread may be disposed between the needle unit and the housing, or between the needle unit and the cartridge.

The thread may be arranged to couple the needle unit to the cartridge and/or the housing after rotation of the needle unit.

In some embodiments, the housing comprises a cartridge mounting portion that surrounds at least a part of the cartridge, and wherein the thread is arranged between the needle unit and the cartridge mounting portion.

The cartridge mounting portion may comprise the thread and the needle unit may comprise a thread engaging member arranged to engage the thread. For example, the thread engaging member may be a protrusion that engages the thread on the cartridge mounting portion.

Alternatively, the cartridge mounting portion may comprise an external thread, and the needle unit may comprise an internal thread that engages the external thread. In other examples, the needle unit may comprise an external thread, and the cartridge mounting portion may comprise an internal thread that engages the external thread.

The cartridge mounting portion may further comprise a groove leading into the thread, and the groove may be arranged such that during movement of the needle unit the needle unit moves linearly before the thread rotates the needle unit. In this way, as the actuator pushes the needle unit the thread engaging member moves along the groove and then into the thread, so that the needle unit initially moves linearly and is then rotated.

The needle may comprise a needle axis, and the needle unit may be adapted to rotate about the needle axis.

In some embodiments, the needle sleeve covers the needle until the needle sleeve has pushed the needle unit into engagement with the cartridge. From this position, further movement of the needle sleeve exposes the needle for injecting a patient. The injection device may further include a spring arranged to urge needle sleeve into an extended position so that after use the needle sleeve slides out of the housing to cover the needle.

In some embodiments, the needle sleeve may be adapted to disengage from the needle unit after the needle unit has rotated such that the needle sleeve can move independently of the needle unit. In this way, an initial movement of the needle sleeve into the housing pushes the needle unit into engagement with the cartridge, and during this movement the needle is rotated so that the needle sleeve disengages from the needle unit and can continue to move into the housing independently of the needle unit.

Movement of the needle sleeve into the housing after the needle unit has been rotated may act to trigger release of the medicament. For example, the movement of the needle sleeve into the housing may cause a piston drive mechanism to drive a piston into the cartridge to expel medicament from the needle. In one example, the piston drive mechanism includes a spring, a plunger, and a catch that holds the spring and plunger in a pre-loaded state. Movement of the needle sleeve into the housing releases the catch so that the spring urges the plunger into the cartridge to dispense medicament.

The needle sleeve may comprise a flange that engages the needle unit, and the needle unit may comprise a recess arranged such that after the needle unit has been rotated the flange is aligned with the recess. In this way, the needle sleeve can move over the needle unit.

Alternatively, the needle sleeve may comprise a helical engaging member and the needle unit may comprise a protrusion that engages the helical engaging member, and the helical engaging member may be arranged such that rotation of the needle unit moves the protrusion out of engagement with the helical engaging member. In this way, the needle sleeve can move over the needle unit.

The needle sleeve may comprise a groove and the needle unit may comprise a protrusion arranged to be received in the groove such that the needle sleeve pushes the needle unit via the protrusion, and the groove may comprise a circumferential portion to permit rotation of the needle unit relative to the needle sleeve. In this way, the needle unit is able to rotate relative to the needle sleeve as it is pushed into the housing.

The groove may further comprise a movement portion arranged to permit the needle sleeve to slide into the housing after rotation of the needle unit.

The cartridge may contain a medicament in the reservoir.

According to another aspect, a method of using an injector device is disclosed. The injector device comprises a cartridge having a reservoir for medicament, a needle unit comprising a needle that is sealed from the reservoir prior to use of the injector device, and a slidably mounted needle sleeve. The method includes sliding the needle sleeve into the housing such that the
    needle sleeve engages the needle unit and pushes the needle unit into engagement with the cartridge such that the needle moves into fluid communication with the reservoir, and rotating the needle unit relative to the cartridge as the needle unit is pushed into engagement with the cartridge.

The injector device includes a cartridge with a reservoir for medicament that is initially sealed from a needle, and a mechanism for moving the needle into fluid communication with the reservoir prior to use.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1A:
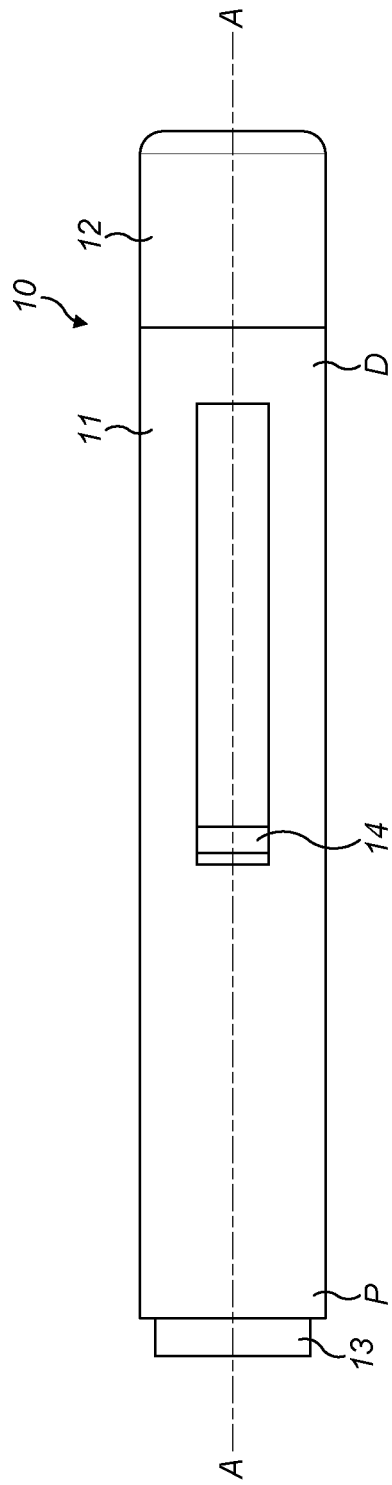
FIG. 1A is a schematic side view of an injector device that embodies the invention, and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
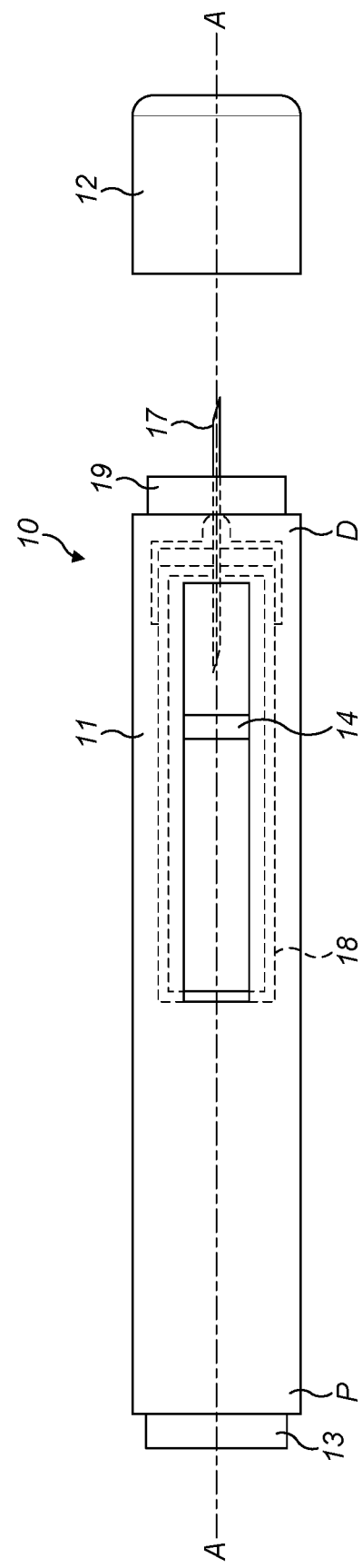
FIG. 1B is a schematic side view of the injector device of FIG. 1A, with the cap removed from the housing.

According to some embodiments of the present disclosure, an exemplary drug delivery device 10 is shown in FIGS. 1A and 1B. The device 10, as described above, is configured to inject a medicament into a patient's body. The device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove the cap 12 from the housing 11 before the device 10 can be operated.

As shown, the housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

The device 10 can also include a needle sleeve 19 coupled to the housing 11 to permit movement of the sleeve 19 relative to the housing 11. For example, the sleeve 19 can move in a longitudinal direction parallel to longitudinal axis A-A. Specifically, movement of the sleeve 19 in a proximal direction can permit a needle 17 to extend from distal region D of the housing 11.

Insertion of the needle 17 can occur via several mechanisms. For example, the needle 17 may be fixedly located relative to the housing 11 and initially be located within an extended needle sleeve 19. Proximal movement of the sleeve 19 by placing a distal end of the sleeve 19 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 19.

Another form of insertion is "automated", whereby the needle 17 moves relative to the housing 11. Such insertion can be triggered by movement of the sleeve 19 or by another form of activation, such as, for example, a button 13. As shown in FIGS. 1A and 1B, the button 13 is located at a proximal end of the housing 11. However, in other embodiments, the button 13 could be located on a side of the housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through the needle 17. In some embodiments, a drive spring (not shown) is under compression before the device 10 is activated. A proximal end of the drive spring can be fixed within proximal region P of the housing 11, and a distal end of the drive spring can be configured to apply a compressive force to a proximal surface of the piston 14. Following activation, at least part of the energy stored in the drive spring can be applied to the proximal surface of the piston 14. This compressive force can act on the piston 14 to move it in a distal direction. Such distal movement acts to compress the liquid medicament within the cartridge 18, forcing it out of the needle 17.

Following injection, the needle 17 can be retracted within the sleeve 19 or the housing 11. Retraction can occur when the sleeve 19 moves distally as a user removes the device 10 from a patient's body. This can occur as the needle 17 remains fixedly located relative to the housing 11. Once a distal end of the sleeve 19 has moved past a distal end of the needle 17, and the needle 17 is covered, the sleeve 19 can be locked. Such locking can include locking any proximal movement of the sleeve 19 relative to the housing 11.

Another form of needle retraction can occur if the needle 17 is moved relative to the housing 11. Such movement can occur if the cartridge 18 within the housing 11 is moved in a proximal direction relative to the housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between the needle 17 and the housing 11 can be locked with a locking mechanism. In addition, the button 13 or other components of the device 10 can be locked as required.

Figure 2:
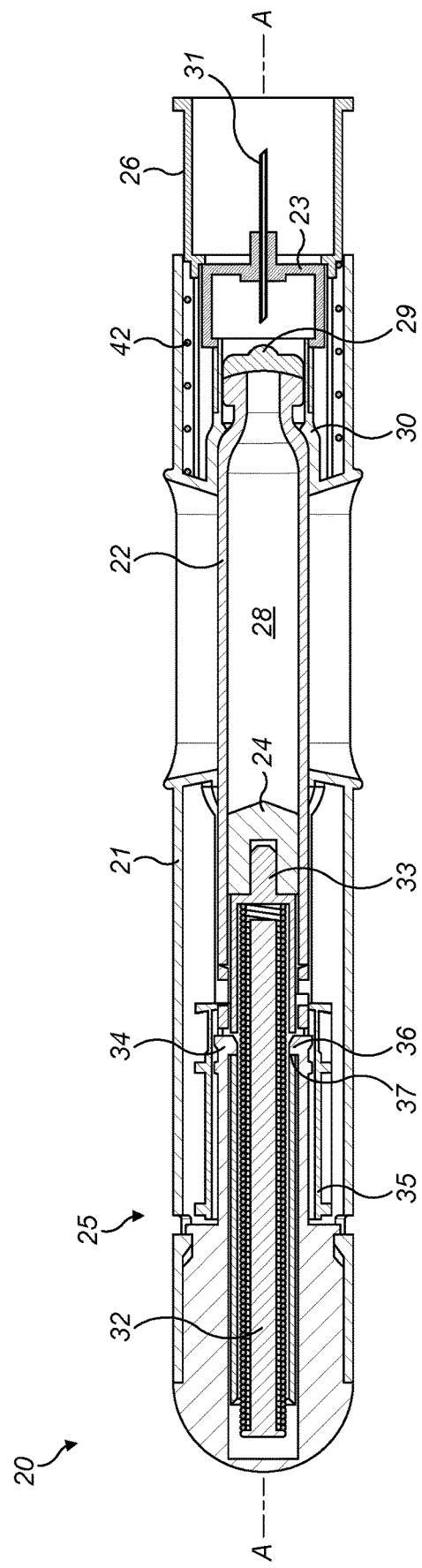
FIG. 2 is a cross-sectional view of an injector device.

FIG. 2 illustrates an example injector device 20 having a housing 21, a cartridge 22, and a needle unit 23. The injector device 20 further includes a piston 24, a piston drive mechanism 25, and a needle sleeve 26.

The cartridge 22 defines a reservoir 28 that contains a medicament and is mounted within the housing 21. A distal end D of the cartridge 22 is sealed by an end cap 29. A cartridge mounting portion 30 of the housing 21 supports the cartridge 22. As illustrated, a part of the cartridge mounting portion 30 is tubular and surrounds the distal end of the cartridge 22. This tubular part of the cartridge mounting portion 30 has an external surface disposed within the housing 21.

As shown in FIG. 2, in an initial condition the needle 31 of the needle unit 23 is spaced from the end cap 29 at the distal end of the cartridge 22 such that the reservoir 28 is sealed from the needle 31. Before or during use of the injector device 20 the needle unit 23 is moved into engagement with the distal end of the cartridge 22 such that the needle 31 pierces the end cap 29 of the cartridge 22. In this way, the needle 31 is placed in fluid communication with the reservoir 28 and medicament can be expelled from the reservoir 28 via the needle 31, as explained further hereinafter.

In the initial condition, illustrated in FIG. 2, the piston 24 is disposed at a proximal end of the reservoir 28 in the cartridge 22, and the piston drive mechanism 25 is disposed in the proximal end of the housing 21. The piston drive mechanism 25 comprises a spring 32, a plunger 33, and a catch 34. The spring 32 is arranged to urge the plunger 33 against the piston 24 and into the cartridge 22 to expel medicament from the reservoir 28 during use. In the initial condition before use, as illustrated, the spring 32 is held in a compressed state by a catch 34. Specifically, the catch 34 holds the plunger 33, which holds the spring 32 in a compressed state such that no force is applied to the piston 24. In this state, the piston drive mechanism 25 is pre-loaded.

As explained further hereinafter, the injector device 20 is actuated by an actuator, in this example the needle sleeve 26 that is rotationally and slidably movable within the housing 21 and protrudes from the distal end of the housing 21. In this way, during use, the needle sleeve 26 is placed against the user's skin and the injector device 20 is pushed towards the user's skin while holding the housing 21, this moves the needle sleeve 26 in an axial proximal direction, into the housing 21.

In other examples, the actuator may be a lever, or a button, or a drive mechanism, for example a motor, that moves the needle sleeve 26 in an axial direction into the housing 21.

The needle sleeve 26 acts to release the catch 34 once the needle sleeve 26 has moved into the housing 21 in a proximal direction. Once the catch 34 is released, the spring 32 urges the plunger 33 against the piston 24 and into the reservoir 28.

As illustrated in FIG. 2, the catch 34 may include a tubular element 35 that surrounds the plunger 33 and spring 32. The tubular element 35 includes protrusions 36 that engage recesses 37 in the plunger 33, such that in the position illustrated in FIG. 2 the plunger 33 is prevented from moving in a distal direction by the protrusions 36 and the recesses 37.

As the needle sleeve 26 is moved proximally into the housing 21, an end of the needle sleeve 26 engages the tubular element 35, causing the tubular element 35 to rotate about the axis A of the injector device 20. This rotation causes the protrusions 36 to disengage from the recesses 37, thereby releasing the plunger 33, which then moves under the force of the spring 32 into the reservoir 28.

In one example, the end of the needle sleeve 26 that engages the tubular element 35 may comprise a chamfer (i.e.

angled edge) that engages a protrusion on the tubular element 35 to cause the rotation. In other examples, the tubular element 35 may comprise a chamfer (i.e. angled edge) that is engaged by a protrusion on the needle sleeve 26 to cause the rotation.

In other examples, the catch 34 may comprise arms that include the protrusions that engage the plunger 33. In this case, the needle sleeve 26 might deflect the arms by lifting them to disengage the protrusions from the recesses, thereby releasing the plunger 33.

A biasing member, for example a spring 42, may be arranged to act between the housing 21 and the needle sleeve 26 to urge the needle sleeve 26 in a distal direction so that it protrudes from the distal end of the housing 21.

Before or during use, the needle unit 23 is combined with the cartridge 22 before the catch 34 is released. As explained below, movement of the needle sleeve 26 in an axial proximal direction initially causes the needle unit 23 to engage the distal end of the cartridge 22, and further movement of the needle sleeve 26 releases the catch 34 so that plunger 33 begins delivery of the medicament via the needle 31.

Figure 3A:
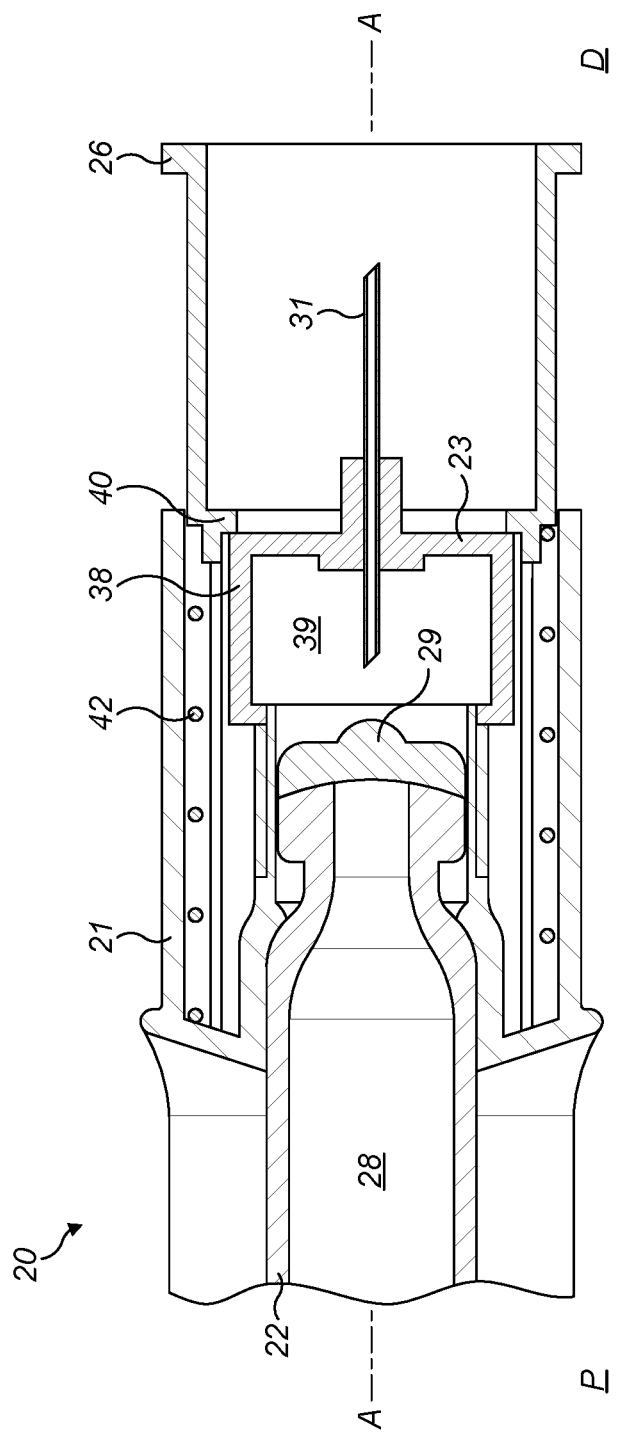
FIGS. 3A to 3C are cross-sectional views of the needle-end of the injector device, showing stages of operation of the injector device.
Figure 3B:
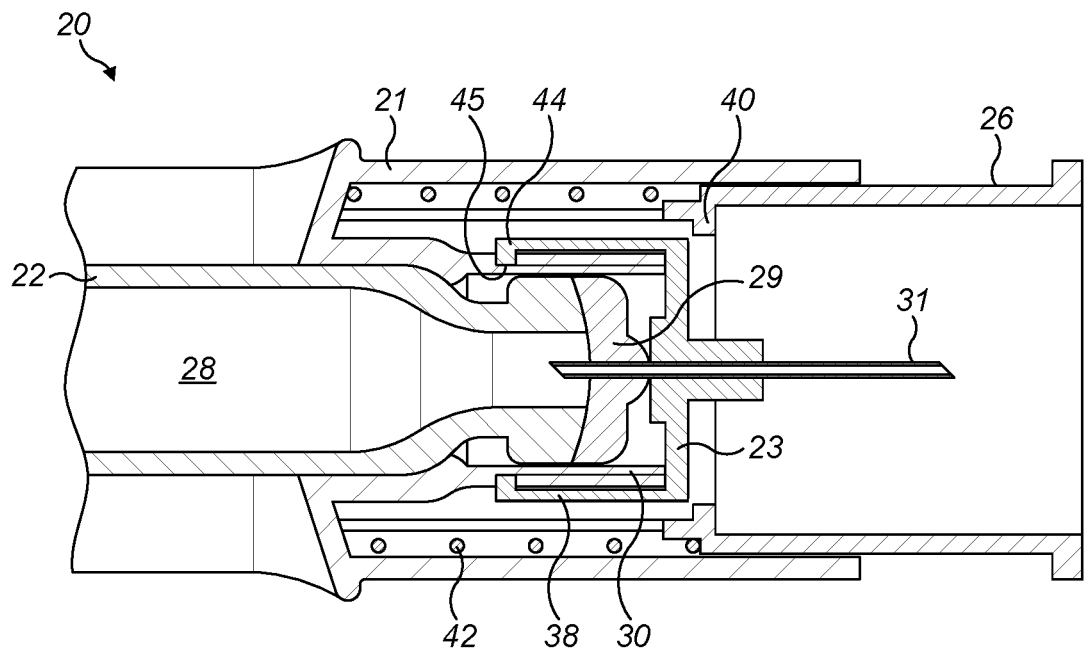
Figure 3C:
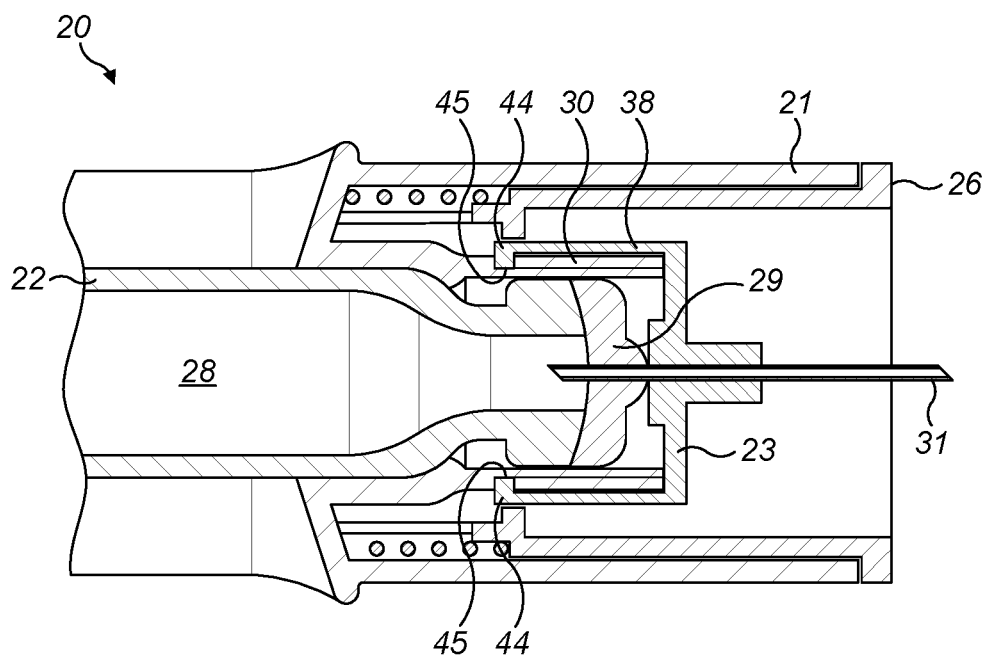

FIGS. 3A to 3C illustrate operation of the injector device 20. In the initial state, shown in FIG. 3A, the needle sleeve 26 is in an extended state protruding from the distal end of the housing 21. The spring 42 urges the needle sleeve 26 in a distal direction. As illustrated, the needle 31, supported by the needle unit 23, is spaced from the end cap 29 of the cartridge 22 so that the reservoir 28 is sealed from the needle 31. The needle 31 is centrally located such that it is aligned with the axis A of the injector device 20. A distal end of the needle 31 is adapted to pierce a user's skin, and a proximal end of the needle 31 is adapted to pierce the end cap 29 of the cartridge 22 when the needle unit 23 engages the cartridge 22.

As illustrated, the needle unit 23 includes a needle body 38 that supports the needle 31 and defines a recess 39 facing proximally in the housing 21. As illustrated, the needle sleeve 26 comprises an annular flange 40 that engages a distal end of the needle body 38, and the proximal end of the needle body 38 engages the cartridge mounting portion 30 of the housing 21.

Specifically, in this example the needle body 38 is threadingly engaged with the cartridge mounting portion 30. The outer surface of the cartridge mounting portion 30 comprises an external thread, and the needle body 38 comprises an internal thread within the recess 39. In the initial condition, the cartridge mounting portion 30 and needle body 38 are partially threadingly engaged at a start of the thread, such that the needle 31 is spaced from the end cap 29 of the cartridge 22.

The needle sleeve 26 is mounted in the housing 21 such that it can slide in an axial direction, but cannot rotate. The needle unit 23 is mounted between the needle sleeve 26 and the housing 21 such that it can rotate about the longitudinal axis A of the injector device 20, and can move in an axial direction. The cartridge 22 is mounted to the cartridge mounting portion 30 such that the position of the cartridge 22 is fixed within the housing 21 and cannot rotate.

In this way, during use of the injector device the distal end of the needle sleeve 26 is placed against a user's skin and pushed down. This causes the needle sleeve 26 to move in a proximal direction into the housing 21 as illustrated in FIGS. 3B and 3C.

FIG. 3B shows an intermediate position of the needle sleeve 26 during use. As shown, movement of the needle sleeve 26 into the housing 21 has moved the needle unit 23 into engagement with the cartridge mounting portion 30, and the needle 31 has pierced the end cap 29 of the cartridge 22, placing the needle in fluid communication with the reservoir 28. The annular flange 40 of the needle sleeve 26 has pushed the needle body 38, so that the needle sleeve 26 and needle unit 23 have moved axially into the housing 21 such that needle unit 23 has engaged the cartridge 22.

As explained above, the needle body 38 is threadingly engaged with the cartridge mounting portion 30, and so during the axial movement between the position shown in FIG. 3A and the position shown in FIG. 3B, the needle unit 23 rotates relative to the cartridge 22 and the housing 21. In particular, the needle unit 23 has been rotated about the axis A of the injector device 20, which is aligned to the needle 31.

The thread engagement between the needle body 38 and the cartridge mounting portion 30 may have a high pitch thread, so that a lower force is required to move the needle unit 23 in an axial direction while rotating the needle unit 23. In one example, the needle unit 23 is rotated through approximately 90 degrees during movement from the initial position (FIG. 3A) to the intermediate position (FIG. 3B). In other examples, the needle unit 23 is rotated between 30 degrees and 120 degrees.

Figure 4A:
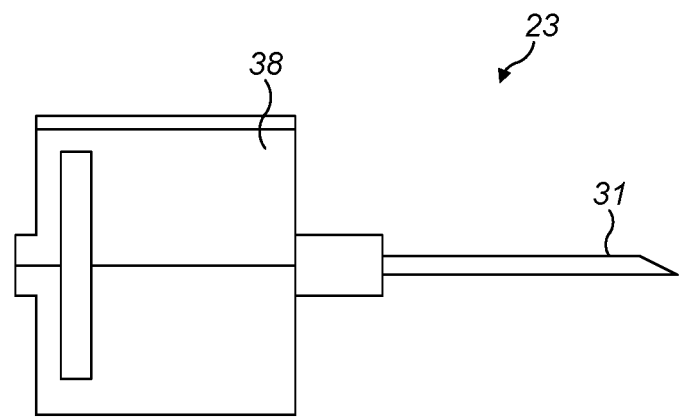
FIGS. 4A and 4B show the needle unit of an injector device.

In this example, the rotation of the needle unit 23 between the initial position (FIG. 3A) and the intermediate position (FIG. 3B) causes the needle sleeve 26 to disengage the needle body 38. Specifically, referring to FIGS. 4A and 4B, the needle body 38 is shaped such that after being rotated the needle sleeve 26 can pass over the needle body 38 in an axial direction.

Figure 4B:
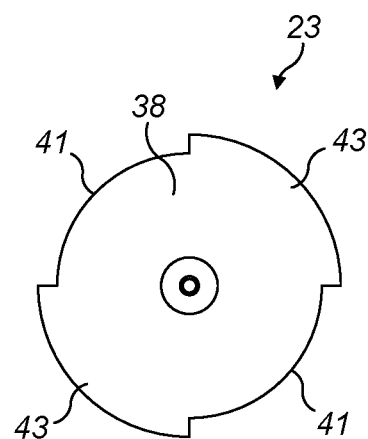

As shown in FIG. 4B, the needle body 38 comprises recesses 41. Similarly, the annular flange 40 of the needle sleeve 26 comprises segments and gaps between segments that correspond to the recesses 41 in the needle body 38. In the initial position (FIG. 3A) the segments of the annular flange 40 of the needle sleeve 26 are aligned with, and engage, the non-recessed parts 43 of the needle body 38 so that the needle sleeve 26 can push the needle unit 23 in an axial direction. Once the needle body 38 has been rotated (due to the thread engagement with the cartridge mounting portion 30 (FIG. 3B)) the segments of the annular flange 40 are aligned with the recesses 41 in the needle body 38, allowing the needle sleeve 26 to pass over the needle body 38 in an axial direction, so that the needle sleeve 26 is able to move axially independently of the needle unit 23.

Therefore, as illustrated in FIG. 3C, after the intermediate position the needle sleeve 26 continues to move in an axial direction, but the needle unit 23 does not. In this way, the needle 31 is exposed and can pierce the skin of the user. In the position of FIG. 3C, movement of the needle sleeve 26 has released the catch (34, see FIG. 2) of the piston drive mechanism (25, see FIG. 2), as previously described with reference to FIG. 2, and the piston (24, see FIG. 2) is urged into the cartridge 22 to deliver medicament via the needle 31.

After use, when the injector device 20 is removed from the skin, the spring 42 urges the needle sleeve 26 back to its initial position so that the needle 31 is covered again.

In the position shown in FIG. 3B, the thread between the needle body 38 and the cartridge mounting portion 30 locks the needle unit 23 onto the cartridge mounting portion 30 of the housing 21.

Additionally, locking members 44 may be provided to lock the needle unit 23 on the cartridge mounting portion 30 of the housing 21. For example, the thread may include an indent 45 to receive a protrusion 44 of the needle body 38 in the position of FIG. 3B, to prevent the needle unit 23 from moving back in the distal direction. Additionally or alternatively, the housing, cartridge mounting portion, and/or the needle body may comprise one or more catches to lock the needle unit in the position illustrated in FIG. 3B and FIG. 3C.

In the example described above, during use the needle unit 23 is initially rotated into engagement with the cartridge mounting portion 30, and then decoupled from the needle sleeve 26 so that the needle sleeve 26 can continue moving axially to release the catch (34, see FIG. 2). However, in alternative examples, the needle unit 23 may be adapted to initially slide axially towards the cartridge 22 as the needle sleeve 26 pushes the needle unit 23, and then the needle unit 23 is rotated to engage with the cartridge mounting portion 30 and disengage from the needle sleeve 26.

Figure 5:
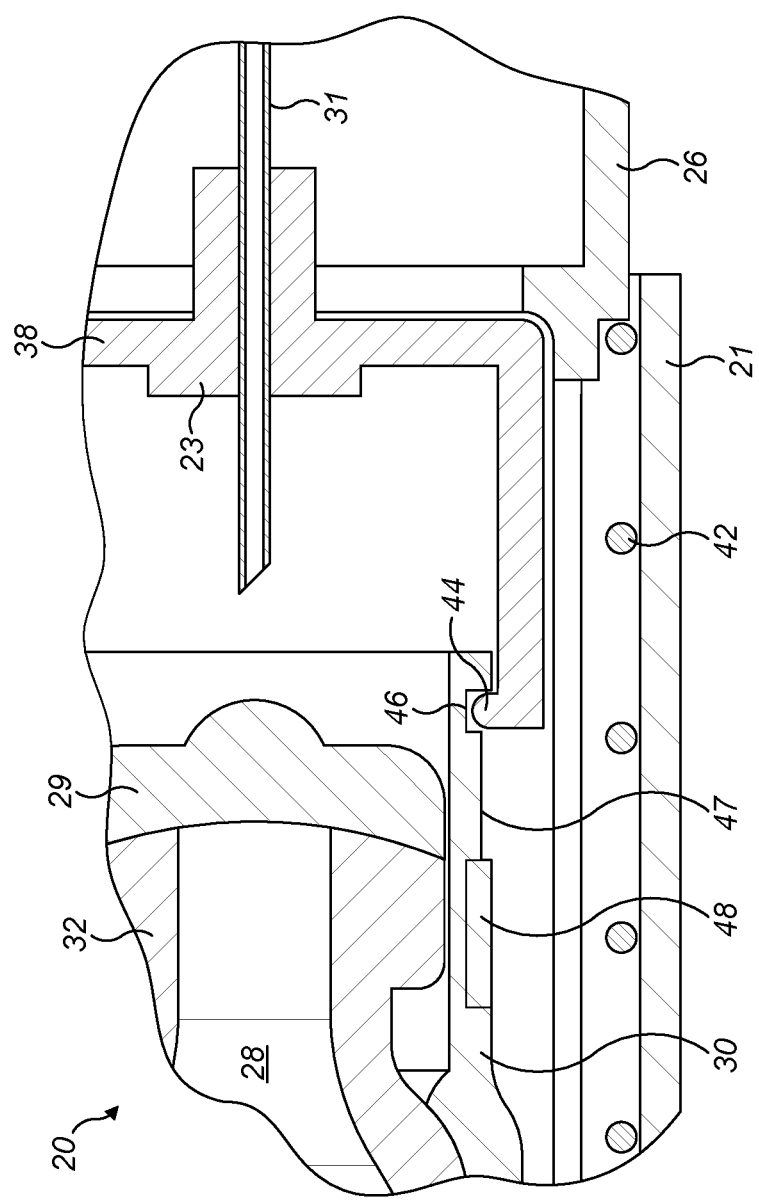
FIG. 5 shows a partial cross-sectional view of the needle-end of an injector device.

FIG. 5 illustrates a further example of the engagement between the cartridge mounting portion 30 and the needle unit 23. In this example, the cartridge mounting portion 30 comprises a notch 46, a groove 47, and a threaded section 48. The needle body 38 comprises a protrusion 44 that engages the notch 46, groove 47, and threaded section 48 in turn as the needle unit 23 is moved axially towards the cartridge 22. FIG. 5 illustrates the initial position of the needle body 38 and needle sleeve 26, equivalent to that shown in FIG. 3A.

During use, the needle sleeve 26 pushes the needle unit 23 in an axial direction, as previously described, and the protrusion 44 is urged out of the notch 46 and into the groove 47, which permits the needle unit 23 to move axially without rotation until the protrusion 44 meets the threaded section 48, which then causes the needle unit 23 to rotate.

During the axial and/or rotational movement the needle 31 has pierced the end cap 29 of the cartridge 22, placing the needle 31 in fluid communication with the reservoir 28. The rotation caused by the threaded section 48 allows the needle sleeve 26 to disengage from the needle body 23 as previously described, so that the needle sleeve 26 can continue its axial movement to release the catch (34, see FIG. 2) and trigger delivery of the medicament. The notch 46 helps to ensure that the spacing between the needle 31 and the cartridge 22 is maintained until a force is applied to the needle sleeve 26 at the beginning of use of the injector device 20.

Figure 6A:
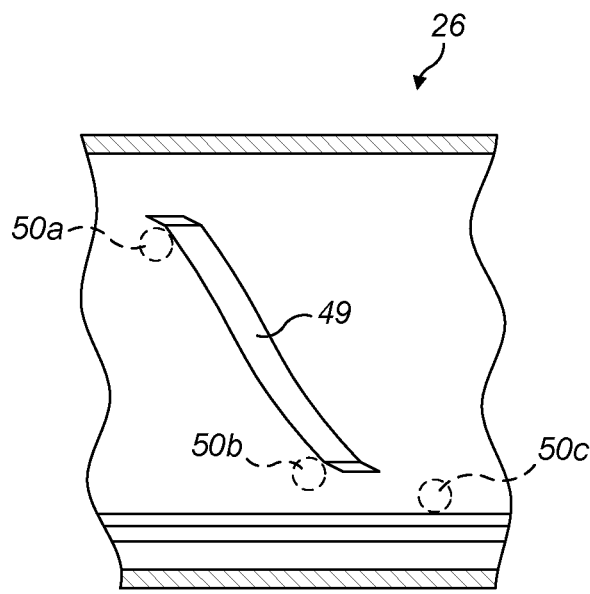
FIGS. 6A and 6B show an alternative needle sleeve for an injector device.
Figure 6B:
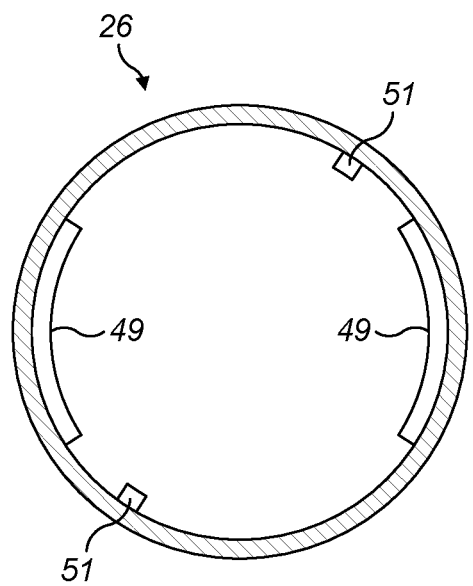

FIGS. 6A and 6B illustrate a further example of the engagement between the needle sleeve 26 and the needle unit 23. In this example, the needle sleeve 26 comprises a helical member 49 on its internal surface. The needle unit 23 includes a protrusion 50 on its outer surface that is engaged by the helical member 49 of the needle sleeve 26 during use. In this way, axial force applied to the needle sleeve 26 is transferred to the needle unit 23 via the helical member 49 and protrusion 50, urging the needle unit 23 into engagement with the cartridge mounting portion 30. The shape of the helical member 49 also aids rotation of the needle unit 23 as the needle sleeve 26 pushes against the protrusion 50. As the needle unit 23 rotates due to the thread engagement between the needle unit 23 and the cartridge mounting portion 30, the protrusion 50 moves out of engagement with the helical member 49 such that the needle sleeve 26 can continue its axial movement without the needle unit 23. In particular, as illustrated in FIG. 6A, during axial movement of the needle sleeve 26 and needle unit 23 the protrusion 50 engages the helical member 49 at positon 50a. Then, as the needle unit 23 rotates, the protrusion 50 moves to position 50b, and then position 50c where the protrusion 50 is not in engagement with the helical member 49 and so the needle sleeve 26 can move further in an axial direction independently of the needle unit 23.

In some examples, the needle sleeve 26 comprises a single helical member 49, and the needle unit 23 comprises a single protrusion 50. However, as illustrated in FIG. 6B, the needle sleeve 26 may comprise two helical members 49 and the needle body 38 correspondingly comprises two protrusions 50. In other examples, the needle sleeve 26 may instead comprise three or more helical members 49.

FIG. 6B also shows optional end stops 51 that the protrusions 50 engage once the desired amount of rotation has been reached, to prevent over-rotation. The end stops 51 are positioned such that the protrusions 50 can pass between the end of the helical member 49 and the end stop 51.

In an alternative example similar to that illustrated in FIGS. 6A and 6B, the needle unit 23 may comprise the one or more helical members 49, and the needle sleeve 26 may comprise the corresponding protrusions 50.

Figure 7:
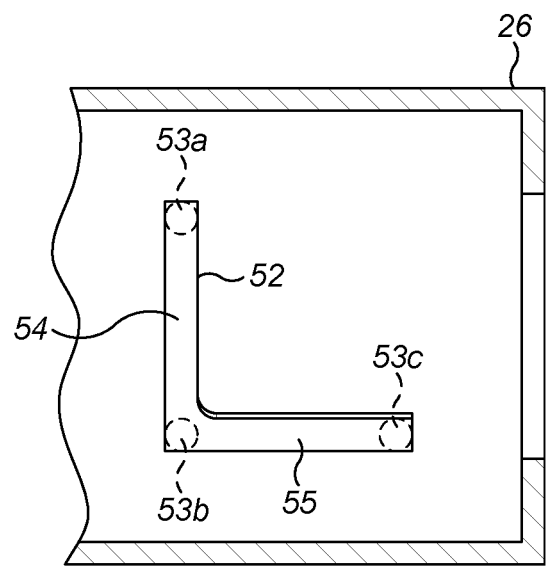
FIG. 7 shows an alternative needle sleeve for an injector device.

FIG. 7 shows an alternative example of the engagement between the needle sleeve 26 and the needle unit 23. In this example, the needle sleeve 26 comprises an 'L' shaped slot 52, and the needle unit 23 comprises a protrusion 53 that engages the 'L' shaped slot 52. The 'L' shaped slot 52 is disposed in the circumferential wall of the needle sleeve 26. As illustrated, the 'L' shaped slot 52 has a circumferential portion 54 extending in a circumferential direction about the needle sleeve 26, and an axial portion 55 extending in an axial direction of the needle sleeve 26.

In an initial position the protrusion 53 is in the location indicated by 53a. In this position, the needle sleeve 26 and needle unit 23 move together in an axial direction as the needle sleeve 26 presses the needle unit 23 via the circumferential portion 54 of the 'L' shaped slot 52 and protrusion 53. Then, as the needle unit 23 is screwed onto the thread of the cartridge mounting portion 30 the protrusion 53 moves to the position indicated by 53b, and from there the needle sleeve 26 is free to move axially independently of the needle unit 23, as the protrusion 53 moves along the axial portion 55 to the position indicated by 55c. In this way, the rotation of the needle unit 23 causes the needle sleeve 26 to disengage from the needle unit 23 so that the needle sleeve 26 can move axially over the needle unit 23 to expose the needle 31 and release the catch (34, see FIG. 2).

Figure 8:
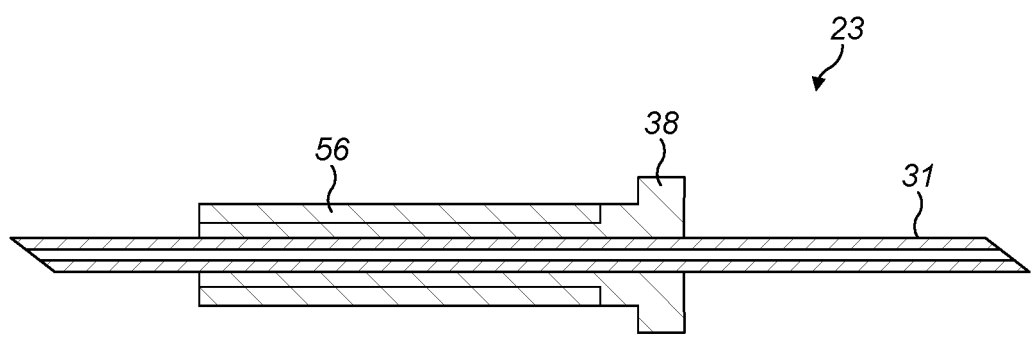
FIG. 8 shows an alternative needle unit for an injector device.

FIG. 8 shows an alternative example needle unit 23. In this example, the needle body 38 comprises an external thread 56 that is arranged to engage with an internal thread on a part of the cartridge mounting portion 30 of the housing 21. This arrangement means that the needle body 38 has a smaller circumference, which reduces the torque required to rotate the needle unit 23 into threaded engagement with the cartridge mounting portion 30.

It will be appreciated that, in various examples, the needle unit 23 may be rotatably coupled to the cartridge mounting portion 30 (as explained previously), to the cartridge 22, or to another part of the injector device 20 that is fixed to the housing 21. For example, the injector device 20 may not include a cartridge mounting portion 30 that extends over the end of the cartridge 22, as illustrated in FIG. 2, and so instead the cartridge 22 may include a thread and the other features described previously.

In the examples described above, the needle sleeve 26 does not rotate as it moves axially into the housing 21. To achieve this, the housing 21 and the needle sleeve 26 comprise a groove and a protrusion, for example a rail, that are engaged with each other to prevent rotation of the needle sleeve 26 relative to the housing 21.

In various examples, elastic stops are disposed between the needle unit 23 and the cartridge 22 or the housing 21, to help prevent overly forceful contact between the needle body 38 and the end cap 29 of the cartridge 22 that could cause damage to the end cap 29.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term, "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A method of using an injector device, the method comprising:
   sliding a needle sleeve of the injector device into a housing of the injector device such that the needle sleeve engages a needle unit of the injector device, pushes the needle unit into engagement with a cartridge of the injector device, and moves a needle of the needle unit into fluid communication with a reservoir of the injector device, and
   rotating the needle unit relative to the cartridge as the needle unit is pushed into engagement with the cartridge.

2. The method of claim 1, wherein sliding the needle sleeve of the injector device into the housing of the injector device comprises placing a distal end of the needle sleeve against a skin of a subject and exerting a downwards force, causing the needle sleeve to move in a proximal direction into the housing of the injector device.

3. The method of claim 1, wherein sliding the needle sleeve of the injector device into the housing of the injector device comprises sliding a protrusion of the needle unit into a groove of the needle sleeve.

4. The method of claim 3, wherein the groove of the needle sleeve comprises an axial portion and a circumferential portion.

5. The method of claim 4, wherein rotating the needle unit relative to the cartridge as the needle unit is pushed into engagement with the cartridge comprises rotating the protrusion of the needle unit along the circumferential portion of the groove of the needle sleeve.

6. The method of claim 1, wherein a reservoir of the injector device contains a medicament.

7. The method of claim 1, wherein the sliding is performed by an actuator.

8. The method of claim 7, wherein the actuator comprises the needle sleeve.

9. The method of claim 1, wherein rotating the needle unit relative to the cartridge comprises rotating the needle unit relative to a threaded engagement between the needle unit and the housing of the injector device or between the needle unit and the cartridge.

10. The method of claim 1, comprising, after rotating the needle unit relative to the cartridge, locking the needle unit to the housing of the injector device using one or more locking members.

11. The method of claim 1, comprising, after rotating the needle unit relative to the cartridge, disengaging the needle sleeve from the needle unit such that the needle sleeve can move independently of the needle unit.

12. The method of claim 1, comprising, after rotating the needle unit relative to the cartridge, moving the needle sleeve into the housing to trigger a release of a medicament contained within the reservoir of the injector device.

13. The method of claim 12, wherein moving the needle sleeve into the housing to trigger the release of the medicament comprises releasing a catch holding a spring and a plunger in a pre-loaded state, so that the spring urges the plunger into the cartridge to dispense medicament.

14. The method of claim 1, comprising, subsequent to engagement of the needle unit with the cartridge, moving the needle shield further to expose the needle for injecting a patient.

15. The method of claim 14, comprising sliding the needle shield out of the housing, into an extended position, to cover the needle.

16. A method of using an injector device, the method comprising:
 placing a distal end of a needle sleeve of the injector device against a skin of a subject and exerting a downward force, causing the needle sleeve to move in a proximal direction into a housing of the injector device;
 sliding the needle sleeve into the housing such that the needle sleeve engages a needle unit of the injector device and pushes the needle unit into engagement with a cartridge of the injector device such that a needle of the needle unit moves into fluid communication with a reservoir of the injector device;
 rotating the needle unit relative to the cartridge as the needle unit is pushed into engagement with the cartridge; and
 disengaging the needle sleeve from the needle unit, so that the needle sleeve continues to move in a proximal direction into the housing of the injector device to trigger a release of a medicament contained within the reservoir of the injector device.

17. The method of claim 16, comprising locking the needle unit to the housing of the injector device using one or more locking members.

18. A method of using an injector device, the method comprising:
 sliding a needle sleeve of the injector device relative to a housing of the injector device, the needle sleeve in engagement with a needle unit of the injector device supporting a needle, such that the needle unit is pushed in a proximal direction into the housing of the injector device; and
 sliding and rotating the needle unit relative to a cartridge of the injector device as the needle unit is pushed in the proximal direction, such that the needle unit is pushed into engagement with the cartridge, moving the needle into fluid communication with a reservoir of the injector device.

19. The method of claim 18, comprising sliding the needle sleeve relative to the housing of the injector device to trigger a release of a medicament contained within the reservoir of the injector device.

\* \* \* \* \*